(12) United States Patent
Blamey et al.

(10) Patent No.: US 7,171,272 B2
(45) Date of Patent: Jan. 30, 2007

(54) SOUND-PROCESSING STRATEGY FOR COCHLEAR IMPLANTS

(75) Inventors: Peter John Blamey, Mt. Waverley (AU); Collette McKay, East Melbourne (AU); Hugh McDermott, Mt. Macedon (AU)

(73) Assignee: University of Melbourne, Melbourne (AU)

(*) Notice: Subject to any disclaimer, the term of this patent is extended or adjusted under 35 U.S.C. 154(b) by 422 days.

(21) Appl. No.: 10/343,396

(22) PCT Filed: Aug. 20, 2001

(86) PCT No.: PCT/AU01/01027

§ 371 (c)(1),
(2), (4) Date: Feb. 21, 2003

(87) PCT Pub. No.: WO02/17678

PCT Pub. Date: Feb. 28, 2002

(65) Prior Publication Data

US 2003/0167077 A1    Sep. 4, 2003

(30) Foreign Application Priority Data

Aug. 21, 2000  (AU) .................... PQ9527

(51) Int. Cl.
*A61N 1/36* (2006.01)
(52) U.S. Cl. ........................................ 607/57
(58) Field of Classification Search ............ 607/55–57
See application file for complete search history.

(56) References Cited

U.S. PATENT DOCUMENTS 4,617,913 A   10/1986  Eddington
5,095,904 A *  3/1992  Seligman et al. ............ 607/57
5,215,085 A    6/1993  Von Wallenberg-Pachaly
5,271,397 A * 12/1993  Seligman et al. ........... 607/137
5,724,433 A    3/1998  Engebretson et al.
6,002,966 A   12/1999  Loeb et al.
6,219,580 B1 * 4/2001  Faltys et al. ................ 607/57
6,728,578 B1 * 4/2004  Voelkel ....................... 607/56

FOREIGN PATENT DOCUMENTS

| AU | 17065/92 A | 1/1993 |
|----|------------|--------|
| EP | 0282 335   | 9/1988 |
| EP | 0282 336   | 9/1988 |

(Continued)

OTHER PUBLICATIONS

European Search Report form EP 01 95 9968.

(Continued)

*Primary Examiner*—George R. Evanisko
*Assistant Examiner*—Michael Kahelin
(74) *Attorney, Agent, or Firm*—Jagtiani +Guttag (57) ABSTRACT

A sound processing method for auditory prostheses, such as cochlear implants, which is adapted to improve the perception of loudness by users, and to improve speech perception. The overall contribution of stimuli to simulated loudness is compared with an estimate of acoustic loudness for a normally hearing listener based on the input sound signal. A weighting is applied to the filter channels to emphasize those frequencies which are most important to speech perception for normal hearing listeners when selecting channels as a basis for stimulation.

8 Claims, 2 Drawing Sheets

FOREIGN PATENT DOCUMENTS

WO        WO 91/03913 A1     3/1991

OTHER PUBLICATIONS

International Search Report dated Oct. 8, 2001; counterpart patent application PCT/AU01/01027 filed Aug. 20, 2001; Publication WO 02/17678; Publication Date Feb. 28, 2002: Inventors: Hugh McDermott et al: Applicant: The University of Melbourne.

Written Opinion dated Nov. 27, 2001; counterpart patent application PCT/AU01/01027 filed Aug. 20, 2001; Publication No. WO 02/17678; Publication Date Feb. 28, 2002; Inventors: Hgh McDermott et al: Applicant: The University of Melbourne.

Applicant's Reponse to Written Opinion dated Feb. 4, 2002; counterpart patent application PCT/AU01/01027 filed Aug. 20, 2001; Publication No. WO 02/17678; Publication Date Feb. 28, 2002; Inventors: Hugh McDermott et al; Applicant: The University of Melbourne.

International Preliminary Examination Report dated Feb. 27, 2002; counterpart patent application PCT/AU01/01027 filed Aug. 20, 2001: Publication No. WO 02/17678; Publication Date Feb. 28, 2002; Inventors: Hugh McDermott et al; Applicant: The University of.

Use of Loudness Model for Hearing Aid Fitting, IV . . . ; British Journal of Audiology, copyright 2000, vol. 34, 165-177pp; written by BCJ Moore (see ISR, and PCT Written Opinion).

\* cited by examiner

SOUND-PROCESSING STRATEGY FOR COCHLEAR IMPLANTS

TECHNICAL FIELD

The present invention relates to a sound processing strategy for use in hearing prosthesis systems, with particular application to cochlear implant systems.

BACKGROUND ART

In cases where individuals have experienced sensorineural deafness, the restoration of hearing sensations to such individuals has been achieved through the use of hearing aids and cochlear implants. Cochlear implants in particular have been in clinical use for many years. A wide variety of different speech processing strategies have been employed in order to process a sound signal into a basis for electrical stimulation via implanted electrode arrays. Some systems have focused upon extracting particular acoustic components of the detected sound signal, which are important to the user's understanding of speech, for example the amplitudes and frequencies of formants, and using these as a basis for generating stimuli. Other approaches have also attempted to utilise the generally tonotopic arrangement of the cochlea, so that each electrode corresponds generally to a particular frequency band.

One such approach, commercially used in speech processors sold by Cochlear Limited, is known as SPEAK. In the SPEAK system, the incoming sound signal is processed to provide an indication of the amplitude of the ambient sound signal in each of a predetermined set of frequency channels, and the channels with the largest amplitudes are selected as the basis for stimulation. In other approaches, the outputs of all channels are used to specify the stimulation patterns, rather than just the channels having the highest short-term amplitudes. The channels are defined by the partially overlapping frequency responses of a bank of band-pass filters. The filters may be implemented using a variety of analog or digital techniques, including the Fast Fourier Transform (FFT). The electrodes corresponding to those channels, determined by a clinical mapping procedure, are selected for activation in each stimulation period and are allocated to the channels according to the tonotopic organization of the cochlear. The rate of stimulation is preferably as high as possible subject to limitations imposed by the processing and power capacity of the external processor and implanted receiver/stimulator unit.

The range of electrical stimulus levels is usually determined by psychophysical measurement of threshold and comfortably loud levels on individual electrodes, using fixed-current pulse trains at the same rate as the stimulus cycle rate of the speech processor output. This may be described as per electrode loudness mapping. The problem with this method of loudness-mapping is that is does not take into consideration the effects of loudness summation when multiple electrodes are activated in quick succession, as they generally are in the output of speech processors.

Although most processing strategies activate a nominal fixed number of electrodes per stimulus cycle, it is important to realise that the actual number of electrodes stimulated in individual cycles is a variable subset of this number, depending on the level and bandwidth of the acoustic stimulus at each point in time. To illustrate this point, a low-level acoustic pure tone will lead to activation of a single electrode, and the electrical level on this electrode must be at least equal to the psychophysical threshold measured individually for that electrode to be audible. In contrast, a low level broad-band noise may activate (for example) eight electrodes in a stimulus cycle. If each of these eight electrodes are activated close to their individual psychophysical thresholds, as may occur with existing systems, then the resultant loudness will not be close to threshold loudness as intended, but will be closer to the maximum comfortable loudness.

This loudness summation leads to the situation that the output of the processor is too loud, even though the individual levels on each electrode do not exceed a comfortable loudness. Various practical methods have been employed to attempt to overcome this problem, including a global reduction of the upper level limit on each electrode, or the use of complex input signals to set the range of individual levels across electrodes. These methods, although alleviating the discomfort of implant users for loud sounds, do not address a second important issue, and that is the impact of loudness summation on speech perception.

Amplitude envelope fluctuations of a speech signal provide vital cues for speech perception, especially for those people who are less able to make use of spectral cues in the signal (for example, those with few active electrodes or poor electrode discrimination ability). Therefore it is important that the changes in acoustic intensity from moment to moment in a speech signal are accurately conveyed as the appropriate perceptual loudness changes to the implantee. The present loudness coding methods, whereby the acoustic output of a filter is mapped to a fixed range of electrical levels (however determined) on its corresponding electrode, lead inevitably to a perceptual distortion of the amplitude envelope shape because these methods do not take into account the variations from moment to moment of important aspects such as the number of electrodes activated in each stimulus cycle, and the relative loudness contributions from these other electrodes. In summary, the relative loudness of electrically stimulated hearing using present approaches does not accurately convey the relative loudness that a normally-hearing person would hear for the same acoustic input. As well as distorting the perception of the amplitude envelope of the acoustic signal, this effect will lead to narrow-band signals being masked by lower-level broadband noise, thus disrupting the ability of implantees to understand speech in background noise.

Whilst the SPEAK approach has proven successful clinically, it is an object of the present invention to improve sound processing strategies so as to enhance intelligibility of speech and other sounds, for users of cochlear implants. It is a further object of the present invention to improve the perception of loudness provided to users of cochlear implants.

SUMMARY OF THE INVENTION

Broadly, the present invention relates to applying models of sound perception for normal hearing in the sound processing scheme to improve the control of loudness and to provide additional information about sound signals, while ensuring the implant users perceive signals of appropriate loudness. In one aspect the present invention relates to applying shaping algorithms to the amplitudes of the channels after initial analysis to allow further processing of the amplitudes in each channel. The shaping algorithm takes into account the relative importance of each channel for speech perception by normal hearing listeners. The purpose is to not merely emphasise the channels with the largest amplitudes, but to also apply a selective weighting towards those most important for speech perception.

According to another aspect, the input sound signal is processed to determine an overall loudness estimate for a hypothetical listener with normal hearing. After the parameters of the electrical stimuli are determined according to the stimulation scheme employed, the loudness perceived by the implant user with the proposed stimuli is estimated, based on parameters including the previous stimuli applied, and relevant characteristics of the patient's auditory perception with electric stimulation which have been previously determined clinically. If the loudness of the proposed stimuli is not the same as that for a normally hearing person within a predetermined range, then the stimuli are adjusted and the loudness estimated again, until the range is met. This may be termed normalising the overall loudness as perceived by a listener using electric hearing. Preferably, the input values for the electrical stimuli are initially determined using an established sound processing scheme for cochlear implants, such as the SPEAK scheme described above. However other schemes may also be employed, including schemes which generate simultaneous or analog patterns of stimulation, rather than stimulation using sequences of rectangular pulses which do not overlap in time. The intention of this approach is to adjust the electric stimulation so that the overall loudness of the user's percept is comparable to that of a normal hearing listener for the same input sound signal, including taking account of the specific user's characteristics. This approach is particularly applicable when it is desired to produce overall loudness which is not identical to that perceived by a hypothetical normal hearing listener, but has a predetermined relationship to normal loudness. For example, it may be desirable to compress the range of loudness levels perceived using the implant compared with the normal range so as to reduce the effects of background noise, or to enhance speech intelligibility. This approach also provides signals which better emphasise the signals known to be most important to speech perception in normally hearing people.

The present invention also attempts to provide a scheme that can improve the control of not just the overall loudness of signals perceived by cochlear implant users but also to improve the control of the relative loudness of signals presented to implant users, particularly the relative loudness of different components of speech signals, such as phonemes. This is done by using a version of the present scheme which controls the distribution of loudness contributions across frequency or across cochlear position, rather than controlling the overall loudness. This aspect will be described in more detail below.

The above approaches allow for improvement when used with existing implants and processors. However, with an increasing trend to provide more electrodes for possible stimulation, to allow for a higher rate of stimulation, to provide for multiple simultaneous or near simultaneous stimuli, and to provide for stimulation using waveforms that are continuous in time (ie analog stimuli), the above approaches become more important. As the stimulation environment becomes more complex, it is increasingly important to control the overall perceptual effects of stimulation, such as the loudness perceived by the user, to ensure that the full benefits of stimulation with a cochlear implant can be obtained. The present invention will have increased application as more complex schemes are implemented.

DETAILED DESCRIPTION

Illustrative embodiments of the present invention will now be described with reference to the accompanying figures, in which.

The present invention will be described with reference to particular approaches to speech processing. However, it will be appreciated that the present invention can be applied to many different speech processing strategies, as an addition to assist in providing an outcome where the percepts provided to the user are optimal, particularly when many stimuli are applied within a short time interval and/or to multiple electrode positions. Further to this, each aspect of the present invention can be applied to existing speech processing schemes either separately or in combination to enhance the operational characteristics of such schemes.

The scheme described below incorporates the various aspects of the present invention discussed above. The scheme is similar in many respects to the SPEAK system used commercially by Cochlear Limited, and an understanding of the operation of SPEAK will assist in understanding the present invention. The principles of this system are also described in U.S. Pat. No. 5,597,380, the disclosure of which is incorporated herein by reference.

Figure 1:
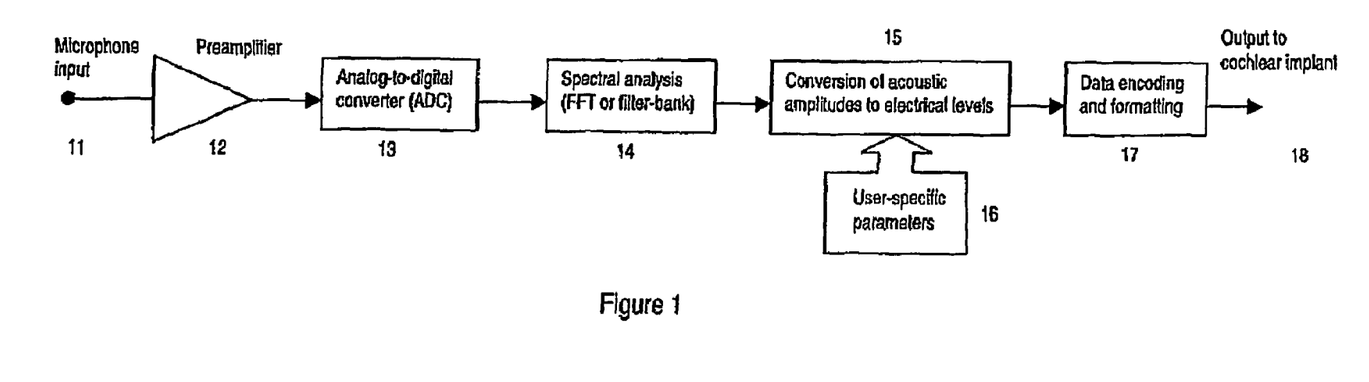
FIG. 1 is a block diagram of prior art arrangement.

FIG. 1 is a functional block diagram showing the main components of a typical existing sound processor for cochlear implants. For convenience, a digital implementation is discussed, however, it will be appreciated that analog (or combined analog/digital) implementations of sound processors are also practical, and are not excluded from the field of the invention.

In FIG. 1, the input is from a microphone 11, via a preamplifier stage 12 to an analog-to-digital converter (ADC) 13. The spectral analysis block 14 is generally implemented by a Fast Fourier Transform (preceded by appropriate windowing of the sampled time-domain input signals), or by a bank of band-pass filters. The output of the spectral analysis block is a set of short-term estimates of the level in a number of discrete or partially overlapping frequency bands. In some existing processing algorithms such as SPEAK or ACE (Advanced Combination Encoder—a SPEAK derivative that uses a generally higher stimulation rate), amplitude information from only a subset of the analysis bands is passed on to the following processing stage. This subset includes the bands with the highest amplitudes. In other schemes, such as CIS (Continuous Interleaved Sampling), amplitudes from all bands are used. However, CIS processors typically have fewer analysis bands than SPEAK or ACE processors. The subsequent processing block 15 converts the amplitude data representing the input spectrum into levels of electric pulses appropriate for the cochlear implant user. A number of user-specific parameters 16 are required. These include data to 'map' the analysis-band frequencies onto the available intra-cochlear electrode positions; the current level and/or pulse width for stimulation on each electrode that is just detectable by the user (the 'T-level'); and the current level and/or pulse width for stimulation on each electrode that is loud but not uncomfortable for the user (the 'C-level').

The amplitude data are converted to current levels 15 for each electrode by a set of independent look-up tables, each containing a non-linear function. For example, for each electrode, the lowest amplitudes are converted to levels near the T-level, and the highest amplitudes are converted to levels near the C-level. The electrode selection and current level data are then encoded digitally 17 and finally transmitted to the cochlear implant 18 so that the desired stimulation of the auditory neurons is produced.

The implementation of the present invention described below may utilise some processes similar to the system described in FIG. 1, but also includes new, more complex processes. It is also envisaged that aspects of the present invention can be applied separately or in combination with the implementation as shown in FIG. 1. It will be understood that the present invention is not specific to any particular hardware implementation, and as such this aspect will not be described as various suitable devices are well known in the art.

In the present invention as in the prior art, the input signal is analysed to estimate the short-term spectrum. This spectrum is then processed by a real-time model, which estimates the distribution of excitation across frequency, or equivalently across cochlear place, as would occur in the ear of a listener with normal hearing. An example of such an estimation process and model will be described in more detail below. In some published models of excitation in normal hearing, the cochlea is modeled as a frequency analyzer based on a bank of partially overlapping band-pass filters, and the excitation pattern is derived from the outputs of these filters. According to this implementation of the present invention, this estimated excitation pattern is converted into a specific loudness function (i.e. the amount of loudness contributed by the excitation in each frequency band, or at each cochlear location). The specific loudness function is then integrated across frequency or cochlear position to estimate the overall loudness of the signal as perceived with normal hearing.

Next, the specific loudness (or excitation) functions are shaped according to the relative importance of each frequency region (e.g. each critical band) for speech perception by normally-hearing individuals. The appropriate shaping is derived from the theory underlying the Speech Intelligibility Index (SII) (Also known as the Articulation Index (AI)), which is well known by those skilled in the art). The critical bands are then sorted in order of largest-to-smallest SII-weighted specific loudness (or excitation). The purpose of this step is to ensure that those parts of the incoming signal which are likely to contain most information about speech are given priority when the electric stimuli are generated.

In other words, the acoustic channels, instead of merely being weighted by absolute amplitudes, are weighted according to their importance to a normal hearing person in speech perception. This approach therefore provides a set of outputs that provide a better speech percept for a user hearing by electric means. The weighted amplitudes are used in the channel-selection process so that the electrodes selected for stimulation are those with the highest amplitudes after the weighting, based on the SII importance function. Additionally, the unweighted loudness function is integrated to provide an overall value for loudness as perceived by a (hypothetical) normal hearing person for the analysis period. The set of stimuli applied to an electric hearing user should provide a loudness approximating this value, in order to match the percepts of a normal hearing person as closely as possible, and accordingly improve the perception of speech and other sounds perceived by the electric hearing user.

To calculate parameters for the electric stimuli, each critical band is treated separately, and in the largest-to-smallest sequence.

The first critical band, having the largest SII-weighted specific loudness, is identified, and the corresponding specific loudness (or excitation) is obtained from the earlier stage of the analysis (i.e. before the SII weighting was applied). An electric stimulus is then constructed that should provide similar specific loudness (or excitation) for the implant user. As the entire processing scheme operates on short-term spectral 'frames', each such stimulus is specified with only two parameters; electrode number and stimulus level. The rate of stimulation is determined by the rate of processing, as in SPEAK or CIS. The active electrode is selected according to the usual 'map' of normal auditory critical band frequencies to electrode positions.

However, the determination of stimulus level is more complicated than in previous schemes. Having selected the active electrode, and having determined the specific loudness that electrode should contribute, the stimulus level is set to provide approximately that specific loudness to the implant user. A model to determine the expected response for the electric hearing user, including parameters specific to that user, is then applied. The model also estimates the spread of excitation around the active electrode. This is because there may be some specific loudness at electrode positions surrounding the first active electrode, even though those other electrodes are not currently activated. In addition, the overall loudness of the stimulation is estimated by integrating the specific loudness function.

The second electrode to be activated in the frame is determined by using the second-largest SII-weighted specific loudness, and then, as described above, the corresponding specific loudness for normal hearing is obtained. The function estimating the distribution of specific loudness across the electrode positions is examined. If the specific loudness associated with the selected electrode is currently less than the specific loudness required to be contributed at that electrode position, a suitable stimulus level is generated to provide the required specific loudness. If there is already sufficient specific loudness at that electrode position, the second electrode is not activated. For example, the spread of excitation from the first active electrode may totally mask the contribution from the second electrode if the second electrode were to be activated at the appropriate level. If the second electrode is activated, the functions estimating the spread of excitation and the distribution of specific loudness across all electrode positions are updated. The estimate of total loudness is also updated.

The process outlined in the preceding three paragraphs is repeated until either the total loudness for the implantee is close to that predicted by the model for normal hearing, or the number of active electrodes reaches some limit, or some other condition is satisfied. In the event that the condition for termination is not satisfied before all the critical bands having non-zero SII-weighted specific loudness have been used, electrode selection can continue based on the specific loudness function itself, or on the levels in the physical spectrum.

The theory underlying the Speech Intelligibility Index (SII) is well established for normally-hearing listeners. For the purposes described above, SII theory needs to be applied to predict the relative importance to speech intelligibility of each frequency band in the incoming spectrum. The importance depends on the level in, as well as the frequency of, each band. The importance function would be set to zero for any frequency band in the short-term spectrum that is below a defined level. This would help distinguish speech from non-speech sounds in the allocation of priorities to the process which selects channels for production of electric stimuli. A further enhancement would be to make that minimum level adaptive, based on the range of levels actually obtained in each spectral band over time. For instance, the minimum level could be set to 30 dB below the maximum level found in the short-term spectrum over the previous few seconds. Another possibility would be to employ a speech/non-speech classifier to influence the way the SII importance is applied in the speech processor.

Similar models of specific loudness, overall loudness, and excitation have been developed for electric stimulation with a cochlear implant. The present processing scheme utilizes one or more of these model outputs depending on which of the three main objectives stated below is under consideration. Thus the preferred implementation of the current processing scheme involves one or more of the following three aspects:

(a) Applying models of loudness for electrical stimulation and for normal hearing to control and optimise the overall loudness of the stimulation applied to the user. This control and optimisation is done by adjusting the parameters of the stimulation in real time to ensure the implant user's perception of loudness is either similar to that of normal hearing, or corresponds to that of normal hearing in an appropriate predetermined relationship.

(b) Applying models of loudness perception and using the estimates of specific loudness (or excitation) obtained therefrom, as well as an overall loudness estimate, to adjust the parameters of the stimulation in real time to produce specific loudness (or excitation) patterns, as estimated to occur in the implant user, that correspond to those of normal hearing in an appropriate predetermined relationship.

(c) Applying models of peripheral neural activity in an acoustically stimulated, normally hearing ear to devise and control appropriately related patterns of electric stimulation to be generated by the cochlear implant.

Models

Several loudness models for normal hearing have been published. One such model has been developed recently by Moore and Glasberg [Auditory Neuroscience, vol. 3, pp 289–3111, 1997; Journal of the Audio Engineering Society, vol. 45, no. 4, pp 224–240, 1997]. A similar model was developed earlier by Zwicker and colleagues. Simplified versions are also described in ISO Recommendation 532: "Method for calculating loudness level". These disclosures are incorporated herein by reference.

A model predicting specific loudness, and thereby total loudness, for electric stimulation for a range of stimulus patterns of pulsatile, constant-current, non-simultaneous stimulation will now be described.

The model receives inputs such as the parameters of each pulse to be delivered to the electrode array. In general such parameters would include the position of pulse delivery site (active electrode number), the electrode configuration (monopolar, bipolar, etc), the pulse onset time, the pulse width, the time separating the phases of the pulse (if the pulse is biphasic) and the current level (or total charge contained in the pulse). Alternatively the model could receive the above parameters combined for the set of all pulses to be generated in each analysis frame. For example, in sound processing schemes like SPEAK and ACE, a set of parameters could be obtained for each scan of the outputs of the band-pass filters, or for each short-term spectral analysis. As outlined previously, each of these scans results in a selection of the electrodes to be activated.

Using the above values specifying the physical parameters of the stimuli to be generated, the model then estimates the contribution made by each pulse to the overall loudness. The pattern of contributions across the available cochlear sites is called the specific loudness function, by analogy to the specific loudness function derived in models of perception with normal hearing (as outlined above). This aspect of the model is based on known psychophysical characteristics of electrical hearing. For example:

Increasing the current or pulse width results in increasing loudness when the cochlear position of the stimulus (ie the electrodes to which the current pulses are delivered) and the rate of stimulation are held constant. The relationship between the loudness and the current (and/or the pulse width) is thought to be approximately a power function or an exponential function. (Note that the product of current and pulse width is the charge per pulse, and the onset times of the pulses are periodic when the stimulation rate is constant. This may enable total charge to be used in the model instead of current level and/or pulse width, and rate instead of pulse onset time).

Increasing the Stimulation rate (i.e. reducing the time interval separating pulse onset times) results in increasing loudness, with a generally larger effect at lower loudness levels.

Increasing the spatial separation between active electrodes may alter the loudness Because the above effects (and others) are known to have substantial interactions with each other, the model may require all of the physical parameters of the pulses over a finite extent of time to estimate each pulse's loudness contribution accurately.

The model also takes into consideration user specific parameters, such as threshold levels (T-levels) and maximum comfort levels (C-levels) and/or other supra-threshold loudness estimates for different rates on all available electrodes, and for different numbers of spatially separate electrodes being activated within a short time (such as within one or several analysis periods, typically about 2–20 ms in total). It is possible that only a subset of these parameters would need to be measured for each implant user with the model using interpolations and extrapolations to extend the measured parameter values to the full range of values required for operation. Also, it is possible that some parameters of the model may have values that do not vary considerably among individual implant users and for such parameters average values would be used in the model rather than separately measured values. Such provisions make the model easily adaptable for each implant user.

During operation this model integrates (or averages) the specific loudness contributions of the pulses to be delivered over an appropriate time interval (e.g. 10 ms, or the analysis period). These integrations are then preferably overlapped in time (e.g. 10 ms averages computed every 5 ms). By integrating the specific loudness contributions across all active electrodes, the model also produces a frequently updated estimate of the total loudness as perceived by the implant user. This estimate includes not only the effects of the most recent pulse delivered to the electrode array but also the (decaying) effects of other pulses delivered within a short time-window centered on that pulse.

In summary, the model predicting specific loudness, and ultimately total loudness, for electric stimulation for a range of stimulus patterns has essentially three aspects: (1) an estimate of the spatial spread of excitation resulting from electric stimulation, derived from the results of psychophysical electric masking studies; (2) estimates of the effects of temporal interactions (including the effects of stimulation rate), which are also available from psychophysical studies; and (3) an estimate of loudness summation for stimulation with multiple pulses delivered to multiple electrodes. By providing estimates of these effects in the current processing scheme, loudness summation is taken into account automatically based on the stimulus pattern being presented. In contrast, sound processing schemes representative of the prior art convert an estimate of the sound intensity in each of a number of frequency bands into a corresponding level of stimulation on a selected electrode without taking account of the effects of pulses delivered on other electrodes or pulses occurring within a short time preceding or following the pulse. In the present invention the explicit accounting for temporal and/or spatial loudness-summation effects for the actual patterns of electric stimulation delivered by the electrodes leads to better intelligibility of speech and other sounds, and improved listening comfort, for the implant user.

Compensation for loudness summation could be applied using a rule based on averaged psychophysical data obtained from measurements obtained from a number of implant users, or a standard rule could be modified to suit the individual implant user. A simple way of obtaining a user-specific estimate of the amount of summation for high loudness levels, would be to obtain C-levels for one or more selected complex (i.e. multi-electrode) stimuli after the C-levels have been obtained in the conventional way for each individual electrode. Temporal effects of loudness summation could be estimated by measuring hearing thresholds (T-levels), and/or levels producing supra-threshold loudness (such as C-levels) for different stimulation rates. Similarly, spatial effects of loudness summation could be estimated by measuring threshold levels and/or levels producing supra-threshold loudness for selected sets of electrodes being activated at different cochlear positions.

Figure 2:
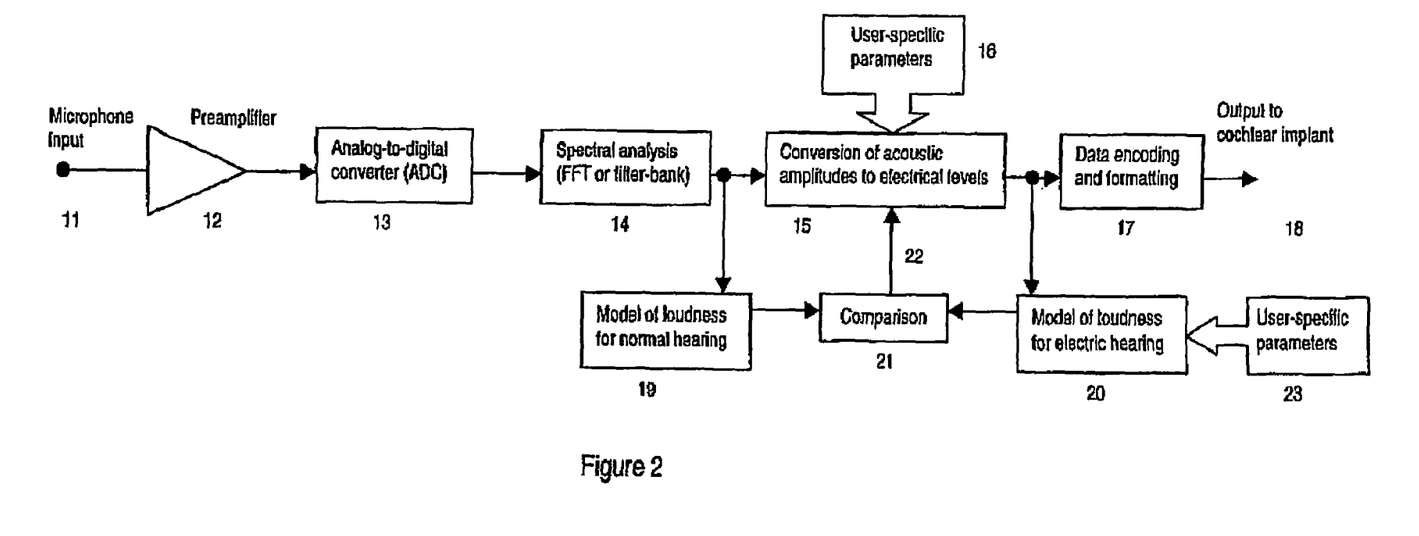
FIG. 2 is a block diagram of a first implementation.

FIG. 2 is a functional block diagram showing how the typical prior-art sound processor of FIG. 1 can be modified to implement a simple version of the inventive processing scheme. The new processing blocks include a loudness estimator for normal hearing 19 and a loudness estimator for electric hearing 20. The loudness estimator for normal hearing is based on a known numerical model, such as that mentioned previously by Moore and Glasberg. It is used to generate an estimate of the loudness of each short-term input spectrum for a hypothetical listener with normal hearing. Similarly, the loudness estimator for electric hearing is based on a novel model of estimating loudness for users of cochlear implants as discussed above, and generates an estimate of the loudness of each short-term output pulse pattern for the individual implanted listener.

Because it is known that the relationship between the physical parameters of the electric stimuli and the loudness perceived by an implant user varies greatly among implant users, user-specific parameters 22 are required in this model. The two loudness estimators 19, 20 produce outputs that are updated periodically or continually. These loudness estimates are compared 21, and a correction signal 23 is generated which aims to equalise the loudness of the electric stimuli to the loudness of the corresponding acoustic input signal. An initial set of parameters specifying the electric stimuli is calculated using a process similar to that in the prior art, and outlined previously. The inventive scheme continually modifies those parameters so as to make the implant user's perception of overall loudness more like that of a hypothetical listener with normal hearing when listening to the same input signals. For example, overall loudness can be adjusted by altering the currents and/or pulse widths of the stimuli either by a constant ratio or by a proportion of the dynamic range (difference between C- and T-levels) on the electrode to which each stimulus is delivered.

Figure 3:
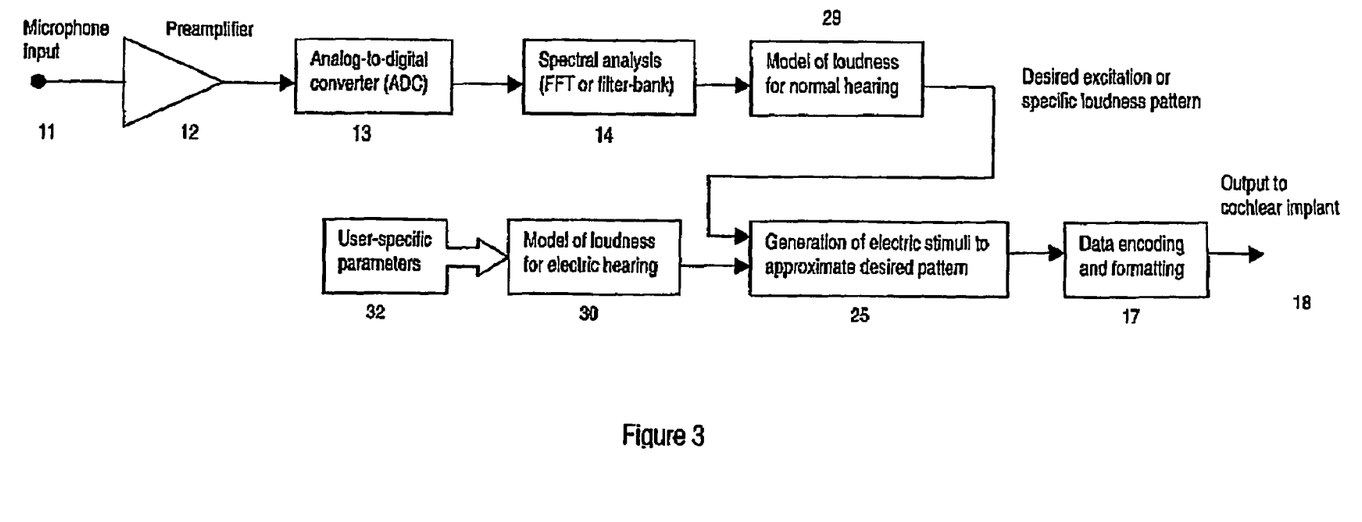
FIG. 3 is a block diagram of a second implementation.

FIG. 3 is a block diagram illustrating a more complex version of the inventive processing scheme. In this version, the conventional processing which converts acoustic amplitudes to current levels in existing sound processors is replaced by model-based processing. The loudness models may therefore be more complicated than those described above. The Moore & Glasberg model for loudness in normal hearing 29 produces an output representing the contribution to the overall loudness made by signals in each of a number of frequency bands. As mentioned above, this is referred to as the specific loudness function. The model also produces an output called the excitation pattern which represents the way activity is distributed through the cochlea in terms of known psychoacoustic properties. Either the specific loudness function, the excitation pattern, or another appropriate output of the model for normal hearing can be used in the inventive sound-processing scheme. The model for loudness in electric hearing 30 is similarly extended to produce outputs representing the specific loudness or the excitation which would result from a given pattern of electric stimuli. As in the simpler scheme (FIG. 2), user-specific parameters 32 are required in this model. In the inventive scheme, the parameters of the electric stimuli to be produced by the cochlear implant are calculated in real time so as to make the specific loudness or excitation in the electrically stimulated cochlea similar to the specific loudness or excitation that would occur in a hypothetical listener with normal hearing when listening to the same input signals. The overall loudness would also be similar, as in the simpler scheme described above. However, the more complex scheme of FIG. 3 has the advantage that the parameters of each electric pulse produced by the implant 25 are specified so that each pulse will contribute an appropriate amount of loudness or excitation, according to the corresponding contributions estimated for each acoustic frequency region by the model of normal hearing. In the simpler scheme of FIG. 2, only the overall loudness level was controlled, without independent adjustments to the parameters of each pulse.

A simplified version of the model producing specific loudness estimates for electric stimulation, suitable for use in a real-time sound processor for cochlear implants, is described as follows. The simplifications depend on two assumptions that have been shown to be applicable for realistic patterns of pulsatile stimulation in many existing implant users. The assumptions are: (1) that the spatial separation between sites of delivery of pulses has a negligible effect on the summation of loudness; and (2) that the loudness contribution of each pulse presented within a stimulation period can be treated independently when estimating the total loudness associated with that period of stimulation. These assumptions mean, for instance, that doubling the pulse rate on a given electrode will result in each pulse contributing approximately half the loudness (relative to the loudness contribution per pulse in the first stimulus) when the overall loudness of the double-rate stimulus is equalised to that of the first stimulus. Furthermore, a similar relationship would hold even when the pulses are distributed among spatially separate electrodes. Thus it is possible to construct an approximate mathematical relationship between loudness and (e.g.) current level by balancing the loudness of a number of stimuli differing in pulse rate and/or electrode position using psychophysical procedures. For example, a known form of this relationship is:

$$\log(L) = (K_1 \times C) + (K_2 \times \exp((C-K_3)/K_4)) + K_5$$

where L is the loudness, C is the current level (specified in the stepwise units used in the prior-art implant devices manufactured by Cochlear Limited, which are related to the electrode current via a fixed, non-linear function approximating a logarithmic function), and the Ks are constants, determined experimentally.

In the inventive sound-processing scheme of FIG. 3, the block 25 generating electric stimuli may employ a look-up table based on the above function to convert the specific loudness estimates from the model for normal hearing 29 into current level data suitable for delivery 17, 18 to the implanted stimulator. In a manner similar to that employed in the prior art, the available electrodes are allocated to frequency bands according to the tonotopic organisation of the cochlea. Using constant-rate pulsatile stimulation, the normal specific-loudness estimates for each frequency band are converted to the specific loudness contributions required at each of the corresponding electrode positions, and then the current levels for the pulses to be delivered to those electrodes are determined from the look-up tables assigned to those electrodes. The total loudness as perceived by the implant user is estimated by summing the specific loudness contributions across all available electrode positions.

The total loudness of the electric stimulation may be limited to a level that is safe and tolerable to the individual implant user. The limiting may be performed by comparing the total loudness estimate with the maximum loudness judged as comfortable by the implant user. If the total loudness estimate exceeds the maximum acceptable loudness at any time, the specific loudness contributions assigned to each of the active electrodes would be reduced in the same proportion (by reducing the current levels of the stimuli) until the total loudness was acceptable. Time constants could be applied to this limiting function to improve its perceived effects. For example, a short attack time (e.g. 5 ms) could be applied to reduce the loudness rapidly when it exceeds the limit, and a longer release time (e.g. 50 ms) could be applied to allow the loudness to increase relatively slowly to its original level when it no longer exceeds the limit. Such limiting techniques are similar to those employed in conventional acoustic hearing aids, where they are well known to those versed in the art.

An alternative model which may be employed in the inventive sound-processing scheme estimates a generalised electric excitation function rather than, or in addition to, the specific loudness pattern. In this model, the electric excitation function, E(p, t, a), is calculated from the physical parameters of the electric stimulus as a non-linear function of position in the cochlea (p), time (t), and the stimulus amplitude (a, which may be represented by the charge per pulse, the current level, and/or the phase duration). E is assumed to be related to the total amount of neural activity at a given time and place. For a localised electric stimulus, such as that produced by a pulse train on a single electrode, the perceived loudness, L(p, a), of the stimulus is a non-linear monotonic function, F, of the electric excitation produced by the stimulus, integrated over a fixed time interval, T:

$$L(p, a) = F\{\int_0^T E(p, t, a) dt\}$$

At a localised cochlear position, the total electric excitation produced by an electric stimulus which has two or more (non-simultaneous) components is equal to the sum of the excitation produced by the individual components. For simultaneous, near-simultaneous, or overlapping electric currents, a weighted summation of electric current may need to be calculated before applying the non-linear transformation to excitation. With conventional pulsatile electric stimulation, in which pulses are delivered to the electrodes sequentially, one suitable form of the non-linear transformation is an exponential decay over time. In the sound processor, the electric excitation pattern can be estimated iteratively by successively transforming the existing electric excitation pattern and adding the excitation pattern contributed by each additional electric pulse. Note that the excitation contributed by a particular pulse may affect the electric excitation pattern at cochlear positions spatially separate from the position at which the pulse was delivered by the electrode. By subtracting the existing electric excitation pattern from the instantaneous pattern required by the sound-processing scheme (calculated from a running analysis of the incoming sound signal), the inventive scheme can determine the optimal parameters of the electric stimuli to be delivered by the implant. For instance, the positions (i.e. selected electrodes) and current levels can be calculated so as to minimise the difference between the desired electric excitation pattern and the estimated existing electric excitation pattern. One advantage of this approach to determining the parameters of the electric stimuli is that more pulses may be delivered by the electrodes to improve the accuracy of the desired excitation pattern in both temporal and spatial dimensions. For example, it may be beneficial to present multiple pulses in a short time interval to one electrode position to provide more detailed information about rapid changes in the incoming signal. Thus, the inventive scheme has the potential to deliver additional information to implant users, compared with the prior art, about detailed aspects of the acoustic signal by controlling spatio-temporal parameters of the stimulation on a relatively fine scale.

Note that in the above descriptions of the inventive sound-processing scheme and its variations, it has been assumed generally that one objective is to ensure that the total loudness (and/or the specific loudness or excitation pattern) perceived by the implant user will be similar to the total loudness (and/or the specific loudness or excitation pattern) perceived by a hypothetical listener with normal hearing. However, it will be appreciated that alternative relationships between the loudness perceived by the implant user and the loudness perceived with normal hearing are possible and are not excluded from the invention. For example, it may be desirable to adjust the specific loudness pattern for the implant user, either on average or adaptively in real-time, so as to maximise speech intelligibility or minimise the loudness of background noise. These adjustments may require the total loudness estimates for the implant user to be held within a range derived from the normal-hearing loudness estimates, or that the relation between the two models' total-loudness estimates follow a predetermined function such as a compressive or expansive relationship.

It will be appreciated that variations and additions are possible within the general inventive concepts disclosed.

The invention claimed is:

1. A method of processing sound signals to generate electrical stimuli for an auditory prosthesis, comprising:
   determining the amplitude within various frequency components of the sound signals within a predefined sample period; and outputting a set of amplitude values for use in determining a set of stimuli to be applied in said prosthesis;

wherein the set of amplitude values are further processed to determine a value for acoustic overall loudness as perceived by a normal hearing listener, and the set of stimuli are processed to determine the perceived overall loudness as perceived by an electric hearing user if the set of stimuli is applied, the set of stimuli being modified if the acoustic overall loudness and the perceived overall loudness do not meet a predefined relationship; and wherein the prosthesis includes an electrode array having multiple electrodes for delivering said stimuli, said stimuli being delivered in discrete stimulation periods, wherein the perceived overall loudness as perceived by an electric hearing listener is determined by a model which assumes that the spatial separation between the electrodes selected for delivering said stimuli does not have a substantial effect upon the perceived overall loudness, and that the loudness contribution of each stimuli can be treated independently when estimating the perceived overall loudness.

2. A speech processor adapted to perform the method of claim 1.

3. An auditory prosthesis adapted to perform the method of claim 1.

4. A computer readable medium having instructions to perform the method of claim 1.

5. A method of processing sound signals in order to generate electrical stimuli for an intracochlear implant with an electrode array having multiple electrodes for delivering stimuli within a cochlea, the method comprising:
(a) determining the amplitude values within various frequency components of the sound signal within a predefined sample period,
(b) outputting a set of amplitude values for use in determining a set of stimuli to be applied in said prosthesis,
(c) processing said amplitude values within frequency components based on a model which calculates a estimated ideal electrical excitation pattern within the cochlea of a normally hearing person as a function of electrode position or frequency component, and time;
(d) converting said ideal electrical excitation pattern into a specific loudness function, which includes a value for the amount of loudness at each electrode position or frequency component;
(e) determining which electrodes are stimulated within the stimulation period based on said specific loudness function is used to determine;
(f) integrating said specific loudness function across all electrode positions or frequency components to determine the estimated overall loudness of said input signal as perceived by a normally hearing listener;
(g) performing step iteratively, starting with the first electrode position corresponding to the frequency component with the largest specific loudness, determining an amplitude for stimuli to be delivered by said first electrode in accordance with a model of electric hearing response, said stimuli being intended to best approximate the specific loudness value determined for the first electrode;
(h) updating said model using the stimuli determined for said first electrode position;
(i) comparing said overall electric loudness of said stimuli determined by said model of electric hearing response with a maximum value which has a specific relationship with said estimated overall loudness, wherein if said overall loudness is less than required for said specific relationship, repeating the process described for the frequency component with the second largest specific loudness, by determining an amplitude for stimuli to be delivered by said second electrode in accordance with said model of electric hearing response, said stimuli being intended to best approximate the specific loudness value determined for the second electrode;
(j) updating said model using the stimuli determined for the first and second electrode positions;
(k) determining the overall electric loudness of said stimuli determined by said model of electric hearing response, wherein if said overall electric loudness value is greater than said maximum value, reducing the amplitude of the stimulus to be delivered by said second electrode, so that said overall electric loudness value is less than or equal to said maximum value; or if said overall electric loudness value is less than said maximum value, repeating steps (i) to (k) using the model as updated for each successive stimuli, until either said maximum value is met or other criteria cause the process to be terminated.

6. A method according to claim 5, wherein after step (b), the values of the specific loudness function are weighted according to their relative importance to speech perception, so as to provide a weighted specific loudness function, and the relative values of this function at frequency components are used in step (e) to determine which electrode position has the largest specific loudness.

7. A method according to claim 6, wherein a minimum threshold is applied to amplitude in each frequency component, so that amplitudes below the minimum threshold are not weighted.

8. A method according to claim 7, wherein said threshold is set dynamically relative to the amplitude in previous periods.

* * * * *